(12) United States Patent
Loewe et al.

(10) Patent No.: US 11,794,135 B2
(45) Date of Patent: Oct. 24, 2023

(54) PRECONFIGURED SINGLE-USE FILTRATION DEVICE

(71) Applicant: SARTORIUS STEDIM BIOTECH GMBH, Goettingen (DE)

(72) Inventors: Thomas Loewe, Goettingen (DE); Andre Dell, Gieboldehausen (DE); Sebastian Handt, Goettingen (DE); Maik Sommer, Seeburg (DE); Thomas Friese, Bleicherode (DE); Mandar Dixit, Medford, NY (US); Bernhard Diel, Dransfeld (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 805 days.

(21) Appl. No.: 16/615,911

(22) PCT Filed: May 15, 2018

(86) PCT No.: PCT/EP2018/062598
§ 371 (c)(1),
(2) Date: Nov. 22, 2019

(87) PCT Pub. No.: WO2018/215246
PCT Pub. Date: Nov. 29, 2018

(65) Prior Publication Data
US 2020/0179837 A1    Jun. 11, 2020

(30) Foreign Application Priority Data
May 22, 2017   (DE) .................... 10 2017 111 133.6

(51) Int. Cl.
B01D 29/52    (2006.01)
B01D 29/56    (2006.01)
(Continued)

(52) U.S. Cl.
CPC ............. B01D 29/52 (2013.01); B01D 29/56 (2013.01); B01D 35/303 (2013.01);
(Continued)

(58) Field of Classification Search
CPC ...... B01D 29/52; B01D 29/56; B01D 35/303; B01D 36/001; B01D 46/521;
(Continued)

(56) References Cited

U.S. PATENT DOCUMENTS 3,785,164 A * 1/1974 Wrenn, Jr. ............. F25B 45/00
62/509
3,909,221 A * 9/1975 Bengtsson ............. B01D 29/96
55/480
(Continued)

FOREIGN PATENT DOCUMENTS

CN    2428143 Y    5/2001
CN    102294064 A   12/2011
(Continued)

*Primary Examiner* — Waqaas Ali
(74) *Attorney, Agent, or Firm* — DILWORTH IP, LLC

(57) ABSTRACT

A single-use filtration device including a plurality of single-use filter capsules connected with each other by rigid lines, of which at least a part is firmly mounted in a raster universally specified by a holder. The filter capsules, in particular as regards the type of filter, type of construction and/or size, and/or the connections of the filter capsules, are preconfigured for a desired filtration process.

24 Claims, 15 Drawing Sheets

(51) Int. Cl.
  *B01D 35/30* (2006.01)
  *B01D 36/00* (2006.01)
  *B01D 46/52* (2006.01)
  *B01D 46/54* (2006.01)

(52) U.S. Cl.
  CPC ......... *B01D 36/001* (2013.01); *B01D 46/521* (2013.01); *B01D 46/543* (2013.01); *B01D 2201/0423* (2013.01); *B01D 2201/16* (2013.01)

(58) Field of Classification Search
  CPC .......... B01D 46/543; B01D 2201/0423; B01D 2201/16; B01D 61/18; B01D 2201/4023; B01D 2313/06; B01D 2313/105; B01D 2313/125; B01D 2313/54; B01D 2313/58; B01D 2317/04; B01D 2317/06; B01D 2317/08; C12M 23/28; C12M 33/14; C12M 47/02; C12M 37/02
  See application file for complete search history.

(56) References Cited

U.S. PATENT DOCUMENTS

| | | | |
|---|---|---|---|
| 4,909,937 | A | 3/1990 | Hoffmann et al. |
| 6,623,631 | B1 | 9/2003 | Graus et al. |
| 8,916,045 | B2 | 12/2014 | Reinbigler et al. |
| 9,045,725 | B2 | 6/2015 | Vogel et al. |
| 10,758,852 | B2 | 9/2020 | Diel |
| 2005/0045552 | A1 | 3/2005 | Tadlock |
| 2008/0269468 | A1 | 10/2008 | Vogel et al. |
| 2012/0248025 | A1 | 10/2012 | Reinbigler et al. |
| 2013/0062266 | A1 | 3/2013 | Horner et al. |
| 2015/0232799 | A1* | 8/2015 | Reif ........................ B01D 71/36 435/297.1 |
| 2015/0252934 | A1 | 9/2015 | Ohta et al. |
| 2015/0283479 | A1* | 10/2015 | Perreault .............. A61L 2/0017 96/6 |
| 2017/0216746 | A1 | 8/2017 | Diel |

FOREIGN PATENT DOCUMENTS

| | | | | |
|---|---|---|---|---|
| CN | 104981284 | A | 10/2015 | |
| CN | 205867747 | U | 1/2017 | |
| DE | 3321038 | C2 | 1/1992 | |
| DE | 19905645 | C1 | 10/2000 | |
| DE | 102015114004 | A1 | 3/2017 | |
| EP | 0051373 | A2 | 5/1982 | |
| EP | 0051373 | A2 * | 5/1982 | ........... B01D 35/303 |
| EP | 2915571 | A1 | 9/2015 | |
| JP | 2012213772 | A | 11/2012 | |
| JP | 2012247257 | A | 12/2012 | |
| JP | 2014509521 | A | 4/2014 | |
| JP | 3191725 | U | 7/2014 | |
| JP | 2015528300 | A | 9/2015 | |
| JP | 2016501125 | A | 1/2016 | |
| WO | 2010009518 | A1 | 1/2010 | |
| WO | 2014088882 | A2 | 6/2014 | |
| WO | 2015058821 | A1 | 4/2015 | |
| WO | 2016033553 | A1 | 3/2016 | |
| WO | 2016045762 | A1 | 3/2016 | |
| WO | 2017032560 | A1 | 3/2017 | |
| WO | WO-2017032560 | A1 * | 3/2017 | ........... B01D 35/303 |

* cited by examiner

PRECONFIGURED SINGLE-USE FILTRATION DEVICE

The invention relates to a preconfigured single-use filtration device, in particular for large-volume filtration processes.

BACKGROUND OF THE INVENTION

In the pharmaceutical production of high-quality active ingredients single-use processes generally are used to an increasing extent due to the high flexibility achievable therewith as well as the saving of time, investments and operating expenditure such as the cleaning, validation and examination of such ingredients. Single-use systems (disposables) used therefor are to be differentiated from reusable systems which cannot simply be disposed of after being used once, but must be cleaned, sterilized and tested again for each further use. Single-use systems are not only desired for small-volume processes, but also for a larger scale, wherein the costs for such systems should not rise unrealistically high.

In processes with bioreactors, which meanwhile are also available as single-use reactors in sizes of 500, 1000 and 2000 liters, there is a demand for media filtration and the filtration conducted after the cell harvest (post-harvest filtration). Proceeding from a total filtration volume of several thousand liters, there is a demand for filters with correspondingly high total filter areas. Such large-scale filtration processes with total filter areas of up to 50 $m^2$ currently are carried out with devices in which filter candles in stainless steel housings are used (e.g. multiround systems). The devices hence still are designed for reuse. This leads to disadvantages such as low flexibility, high cleaning expenditure, production stops due to the cleaning, etc. Corresponding single-use solutions have not been available so far in this order of magnitude.

This was remedied by the completely presterilizable, ready-for-connection and integrity-testable single-use filtration device presented in WO 2017/032560 A1, which is designed for large-volume filtration processes. This single-use filtration device comprises a plurality of single-use filter capsules of a standard size, which are connected with each other by lines and are supported by a rigid holder. It is also possible to use different types of filter capsules within the same device. The lines between the filter capsules can be configured as rigid conduits or be formed by a plurality of uniform inflow and/or outflow devices.

EP 2 915 571 A1 discloses a reusable filtration device with a frame construction for accommodating a plurality of filtration modules. By means of distributor pipes, the individual filtration modules can be connected to form a parallel arrangement, a series arrangement or a combination of both.

From DE 33 21 038 C2 it is known to connect groups of reusable cartridge filters, which each contain a plurality of filter cartridges, in parallel or in series by means of valves.

U.S. Pat. No. 4,909,937 A discloses a reusable filtration device in which individual filter regions can selectively be tested for integrity. For this purpose, there is provided an intermediate region between filter cassettes, which can be filled with a fluid for rinsing, sterilizing, etc. This intermediate region is connected via a connecting piece. All connections and supply lines can be provided with shut-off valves.

From EP 0 051 373 A2 there is known a reusable device for testing filters in the same housing in which the intended filtration process also takes place.

SUMMARY OF THE INVENTION

The superordinate object of the invention consists in providing a single-use filtration device designed for large-volume filtration processes, which can be designed individually for a desired filtration process and its requirements.

This object is achieved by a single-use filtration device with the features of claim 1. Advantageous and expedient embodiments of the single-use filtration device according to the invention are indicated in the sub-claims.

The single-use filtration device according to the invention comprises a plurality of single-use filter capsules connected with each other by rigid lines, of which at least a part is firmly mounted in a raster universally specified by a holder. The filter capsules, in particular as regards the type of filter, type of construction and/or size, and/or the connections of the filter capsules, are preconfigured for a desired filtration process.

The invention is based on the finding that in a large single-use filtration device with a suitable holder, which in principle can accommodate various single-use filter capsules, and with suitable line components that provide for different flow paths for the variable connection of the filter capsules, efficient setups can be realized for carrying out special, individually designed filtration processes. The single-use filtration device according to the invention is optimized in particular in terms of space requirement and handling. Due to the specified raster for the filter capsules, the preferably rigid connecting lines can be very short so that the material and assembly expenditure is minimized. After being equipped with the filter capsules and their connections, the single-use filtration device of modular construction can packed as a whole, in particular be packed hermetically sealed, and subsequently be presterilized (in particular by gamma or hot steam sterilization) so that it can be put into operation immediately after the delivery, without having to add or fix any more components.

According to an advantageous aspect of the invention, at least some of the filter capsules can differ in terms of the type of filter, type of construction and/or size. Different types of construction also will include different types of connection and/or different types of filter construction. Due to the possible choice of the filter capsules, the individual filtration steps can be optimally adapted to the respective requirements (flow rate, permeability, filter area etc.).

What contributes to the variety of the filtration processes to be realized, which are possible with the single-use filtration device according to the invention, also are the lines to be assembled in variable ways. The lines can form a plurality of line branches with associated filter capsules, which are traversed (flow through) one after the other or in parallel.

With the single-use filtration device according to the invention, a plurality of processes or sub-processes can also be carried out at the same time. For such cases it is provided that the lines form at least two separate, mutually independent line branches with associated filter capsules.

According to a particularly preferred embodiment of the invention, the specified raster is a 3×3 raster for a maximum of nine filter capsules, and the lines are preconfigured such that three or less filter capsules arranged in a row of the raster belong to a line branch. On this basis, numerous practical setups can be realized in a compact form. For example, a plurality of single-use filtration units according to the invention can be combined with each other and be connected in parallel or in series. Due to the setup as a raster, a modular combination of a plurality of filtration devices can be realized in a particularly compact form. In general, other rasters, for example 1×2, 1×3, 1×4, 1×5, 1×6, 2×2, 2×3, 2×4, 2×5, 2×6, 3×4, 3×5, 3×6, 4×4, 4×5, 4×6, 5×5, 5×6 or 6×6 rasters, also are conceivable.

The preconfiguration of the single-use filtration device according to the invention already can provide that at least two parallel line branches have a common inlet and/or a common outlet. Joining the line branches before putting the same into operation then is no longer necessary.

In certain setups it can be provided that exclusively sterile filter capsules or exclusively prefilter capsules are used. What is particularly advantageous, however, in general are setups with a combination of at least one sterile filter capsule and at least one prefilter capsule.

According to a particularly advantageous aspect of the invention, a control filter means, preferably in the form of a sterile filter capsule, is arranged in a subsequent line branch. It is the object of the control filter means to ensure as the "last instance" that a sterile filtrate actually is produced. The sterility of the filtrate can be confirmed by an integrity test of the control filter means. This means that when the integrity test of the control filter means is passed, it can safely be assumed that the same has properly fulfilled its function and the filtrate is sterile.

In certain setups it is advantageous to provide one control filter means, preferably in the form of a sterile filter capsule, in each of a plurality of subsequent parallel line branches, in particular when the filter area of only one control filter turns out to be insufficient.

To not only provide for the use of a subsequent control filter means, but also for its integrity independent of the remaining filter capsules of the single-use filtration device without any time-consuming reconstruction or other structural modification of the device, the invention provides that the control filter means is part of an assembly which is provided for a separate integrity test of the control filter means and comprises a sterilizable air filter. When using such an assembly to be fluidically separated from the remaining single-use filtration device, the integrity test can already be carried out as desired already before the intended filtration process (pre-use integrity test), as the sterilizable air filter prevents a contamination of the control filter means still needed, and/or only after the intended filtration process (post-use integrity test).

In particular for such an independent integrity test of the control filter means to be carried out without any reconstruction a setup is advantageous in which an inflow-side first branching member and an outflow-side second branching member are connected to an inflow and to an outflow of the control filter means, respectively, wherein to one of the two free ends of the first branching member the outlet of the sterilizable air filter is connected via an interposed first shut-off valve, wherein to one of the two free ends of the second branching member a waste container optionally is connected via an interposed second shut-off valve, wherein with the other free end of the first branching member the assembly comprising the control filter means, the air filter, the optional waste container, the first and the second shut-off valve and the two branching members is connected with an external port of the single-use filtration device via an interposed third shut-off valve. Here, branching member generally is understood to be any connecting line piece used for realizing a branching, independent of the concrete shape or type of construction of the component. For example, this is meant to include a T-oder Y-shaped connecting line piece or a multi-way valve.

In the setup defined above, the remaining other free end of the second branching member preferably forms a filtrate outlet of the single-use filtration device, which can be closed by a fourth shut-off valve.

An easy accessibility of the control filter means can be ensured in that the control filter means is arranged in an outer line branch.

The control filter means can, however, also be arranged spatially set off outside the specified raster for the filter capsules.

According to another particularly advantageous aspect of the invention a central venting of the entire single-use filtration device is provided. This is achieved by a sterilizable air filter arranged at an upper external port of the single-use filtration device for venting the single-use filtration device. In addition, the integrity of the entire single-use filtration device can be tested via the sterilizable air filter.

Such a venting filter must be sufficiently protected so as not to be blocked. In this connection, blocking should mean that water or another medium forms a kind of film on a fleece supporting the air filter membrane. This results in restrictions concerning the air flow, or an air flow no longer is possible. This problem in particular exists when the air filter membrane and the fleece supporting the air filter membrane are constructed of gamma-sterilizable materials. The invention provides a plurality of possibilities, which possibly can be combined with each other, of protecting the air filter and of making a possible blocking visible in advance so that measures can be taken in good time.

For example, between the external port of the single-use filtration device and the inlet of the air filter a hydrophobic protective filter can be interposed for the protection of the air filter, which prevents the passage of water.

In particular, a configuration of the protective filter as a flat filter is advantageous, which is formed without any supporting fleeces, wherein the protective filter membrane preferably is formed of polyvinylidene fluoride (PVDF), polyethylene (PE), hydrophobic polyethersulfone (PESU) or polytetrafluoroethylene (PTFE). Said materials ensure that blocking largely is avoided by deposition of water on the membrane itself. As no supporting fleeces either are provided intentionally, an otherwise possible film formation is excluded. It hence is ensured that the subsequent air filter does not get in contact with water and thus cannot block, despite the supporting fleeces present there.

The possibilities described below aim at an optical control of the flow path between the external port of the single-use filtration device and the air filter. A possibility for an optical control does not exist in commonly used filtration devices, as pressure-resistant tube materials are not transparent or only so to a limited extent. On the other hand, the possibilities for an optical control presented here enable the operating personnel to recognize ingress of water into the flow path to the air filter and take measures in good time, before the air filter possibly is wetted and impaired in its function.

It can be provided for example that part of the flow path between the external port and the air filter is configured as a sight glass. The generally established term sight glass refers to a transparent tubular portion and is not to be understood in a limiting sense with respect to the choice of material. Beside true glass, a transparent plastic material can also be used for forming the tubular portion.

Another solution consists in arranging at least one indicator in the flow path between the external port and the air filter, which indicator reacts to water, e.g. by a distinctly visible change in color.

Instead of a fabric-reinforced and therefore opaque silicone tube usually employed for connecting the air filter, it can also be provided that part of the flow path between the external port and the air filter is formed by an at least partly transparent silicone tube which is surrounded by a transparent supporting envelope. The envelope ensures that the silicone tube withstands even the high test pressures. Due to the transparency of tube and envelope the passage of water can be recognized.

According to another particularly advantageous aspect, the invention also creates a single-use pipe manifold piece made of a sterilizable plastic material, in particular for a single-use filtration device. The single-use pipe manifold piece according to the invention is formed in one piece and includes at least one branching and/or at least one bend. Branching here is understood to be a branch extending from a main path, and bend is understood to be a very strongly curved or kinked course of the main path, which leads to a significant change in direction of the flow path, e.g. by 90°.

In contrast to known pipe connecting parts, which can be combined to form a multiplex device only by means of additional brackets and many connections which each in turn require seals, the single-use pipe manifold piece according to the invention provides for a much more compact setup of such a device with less connections. In practice, savings of installation space of up to 80% and connection savings of up to 55% are obtained. In addition, the process safety is increased, and the complexity of the assembly is reduced at the same time.

The single-use pipe manifold piece according to the invention preferably is designed so pressure-resistant that it withstands pressures of more than 5 bar, preferably of more than 10 bar.

Preferably, a bursting disk is integrated in the single-use pipe manifold piece according to the invention. Such a bursting disk acts as a predetermined breaking point and in principle can be arranged at any point on the single-use pipe manifold piece, e.g. integrated into one of the inlets/outlets or also into a side wall. It serves to protect the installation from a damaging overpressure/underpressure. In particular, the bursting disk can be arranged between a filtration device and an air filter by means of a T-piece or the like, wherein a branch leads to the bursting disk.

The single-use pipe manifold pieces according to the invention can be joined in a pressure-resistant and non-rotatable way by means of TRI-clamp connections, screw connections or by welding to form an arbitrary compound. Alternatively, sterile connectors can be mounted directly at the open ends of the single-use pipe manifold pieces.

According to a preferred embodiment, at least one bend is formed at an open end of the single-use pipe manifold piece.

The single-use pipe manifold piece according to the invention can also be used for venting an entire single-use filtration device when it is arranged at the top of the device. In this case, the single-use pipe manifold piece is provided with a separate venting outlet which points upwards in the installed position.

According to an advantageous development, the single-use pipe manifold piece is formed of a transparent plastic material in order to be able for example to better observe a venting process.

BRIEF DESCRIPTION OF THE DRAWINGS

Further features and advantages of the invention can be taken from the following description and from the attached drawings to which reference is made. In the drawings.

DETAILED DESCRIPTION OF THE INVENTION

Figure 1:
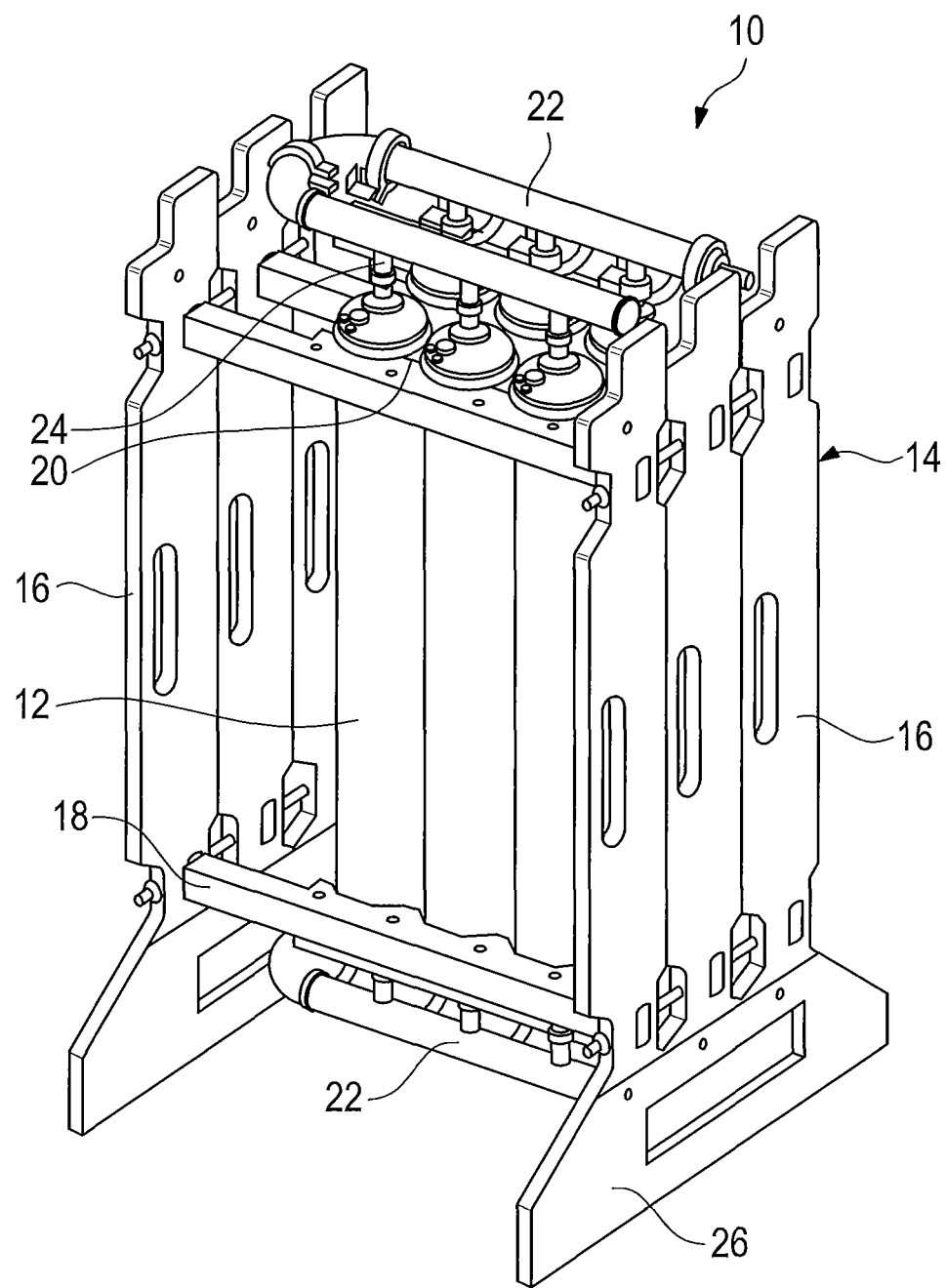
FIG. 1 shows a perspective view of a single-use filtration device.

FIG. 1 shows a single-use filtration device 10 which is similar to the device known from WO 2017/032560 A1. A plurality of filter capsules 12 is held in position in a specified arrangement (raster) by a rigid holder 14. The term "filter capsule" here is to be understood in a general sense and is meant to designate any independently mountable unit comprising at least one filter.

The holder 14 comprises at least two opposite side walls 16 which are connected with each other by transverse struts 18, wherein the side walls 16 can include standing feet 26. On the holder 14, handles (not shown) can also be provided in order to simplify handling. On the transverse struts 18, holding means 20 are provided for the individual filter capsules 12.

The filter capsules 12 are completely or at least for the most part connected with each other by rigid, pressure-resistant conduits 22. The course of the conduits 22 is determined by the intended operation of the filtration device (parallel or series connection of the filter capsules 12), wherein the conduits 22 include the necessary branchings 24 to the individual filter capsules 12. As far as necessary, the conduits 22 are attached to the holder 14.

The essential components of the rigid holder 14, the rigid housings of the filter capsules 12 and the rigid conduits 22 all are preferably formed of the same material. This material and possibly further materials which are used in the device 10 (e.g. for possible flexible tubings) are sterilizable, in particular by means of gamma radiation, and autoclavable. The filtration device 10 thus can be sterilized and packed in the pre-mounted, i.e. ready-to-connect condition.

Figure 2A:
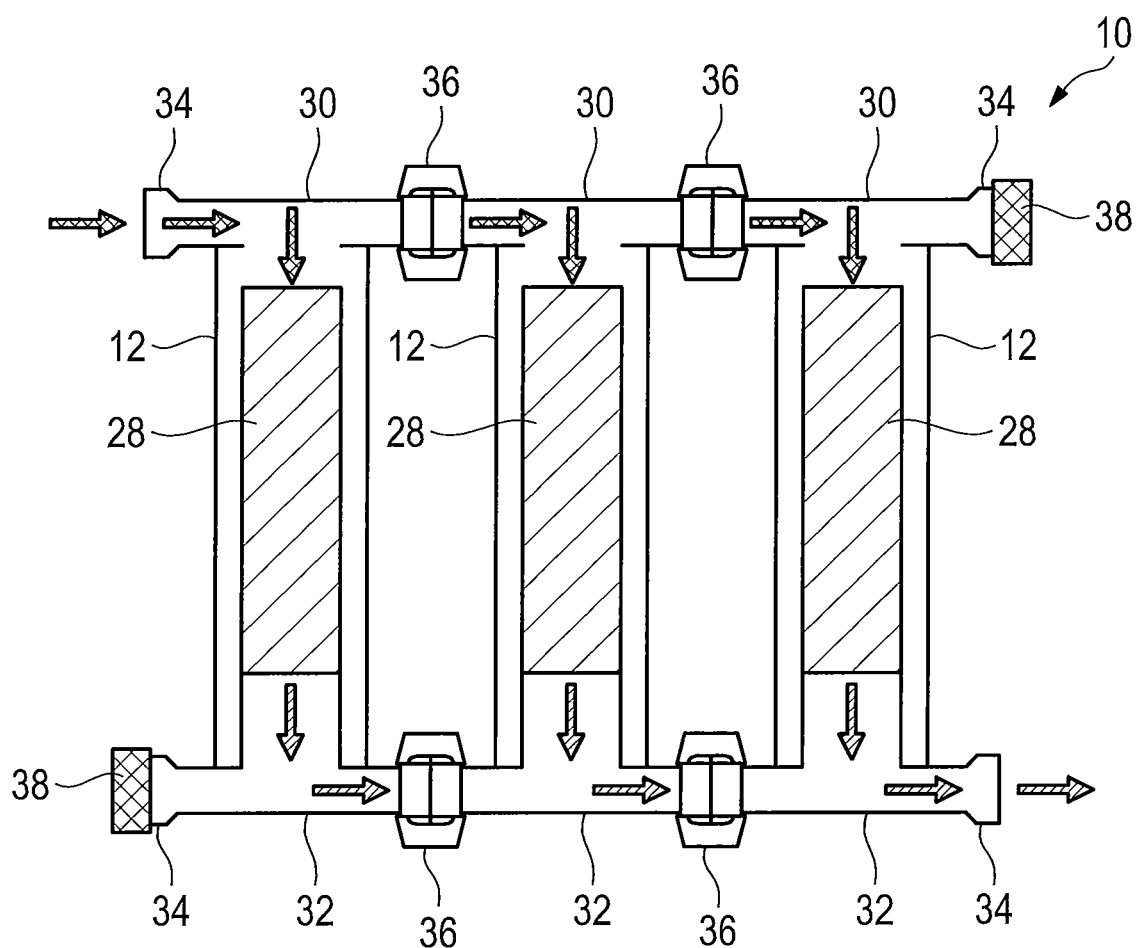
FIGS. 2a to 2d show schematic representations of different variants of a first embodiment of the single-use filtration device according to the invention without a holder in a side view and in a top view, respectively.

FIG. 2a schematically shows another embodiment of the filtration device 10, but without a holder 14. Instead of the conduits 22 and branchings 24 rigid, uniform inflow and outflow devices 32 made of sterilizable, in particular gamma-sterilizable plastic material are provided here. More exactly, for each filter capsule 12, which here is shown with the filter candles 28 accommodated therein, a separate inflow device 30 and a separate outflow device 32 is provided, which are adjusted to the end-face inflow and outflow ports of the respective filter capsule 12. The inflow device 30 and the outflow device 32 either are of completely identical or of at least largely identical construction. Both the inflow device 30 and the outflow device 32 each include two opposite external ports 34. By suitable connection components 36, such as TRI-clamp connections, a plurality of inflow and outflow devices 30, 32 can be connected with each other under controlled conditions. Between the inflow and outflow devices 30, 32 a seal (not shown) each is provided therefor. Alternatively, the inflow and outflow devices 30, 32 can also be connected for example by clamps, screws or welding. In this way, any number of filter capsules 12 can be joined together. The external ports 34 not needed are sealed by suitable closures 38. These closures 38 or also blind caps likewise are mounted by means of suitable connection components 36. The inflow and outflow devices 30, 32 can be formed integrally, as a kit or as a prefabricated unit. In particular, a plurality of inflow devices 30 and/or outflow devices 32 can be formed integrally as one piece or be pre-mounted, before they are mounted on the filter capsules 12.

In particular in the configuration with a plurality of interconnected inflow devices 30 and/or outflow devices 32, which can also be referred to as series-connected lids, numerous advantages are obtained as compared to other line connections. In particular, no or at least less large conduits 22 and connection components 36 are necessary. The series-connected lids provide for the parallel flow to a plurality of filter capsules 12 and can be combined as desired in terms of the sizes and types of construction of the filter capsules 12. In general, the series-connected lids provide for a more compact, smaller size of the single-use filtration device 10, also because the holder 14 can be of smaller size. As less components are needed when using series-connected lids, the single-use filtration device 10 in general is more environmentally friendly and is easier to assemble.

FIGS. 2b to 10 schematically show further examples of various setups of a single-use filtration device 10, wherein the same reference numerals are used for corresponding components.

In all embodiments, at least the filter capsules 12 provided for the essential filtration processes are arranged in a raster specified by the holder 14 or another holding device. The filter capsules 12 themselves (type of filter, type of construction, size, etc.) and the connections of the filter capsules 12 among each other by means of the conduits 22 or inflow and outflow devices 30, 32 can be freely preconfigured. The conduits 22 or inflow and outflow devices 30, 32 define the course of the flow through the individual filter capsules 12, wherein various line branches can be formed, which are traversed (flow through) one after the other or in parallel. Furthermore, all embodiments have in common that they can be delivered by a supplier to a customer in the sterilized condition and ready for use. For this purpose, the single-use filtration devices for example are packed and subsequently sterilized by means of gamma radiation.

First of all, the different setups as such will be briefly explained, before various aspects of the invention and certain possibilities of application are discussed.

Figure 2B:
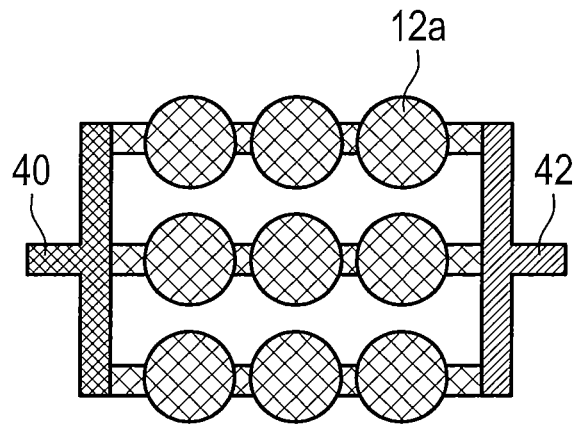
Figure 2C:
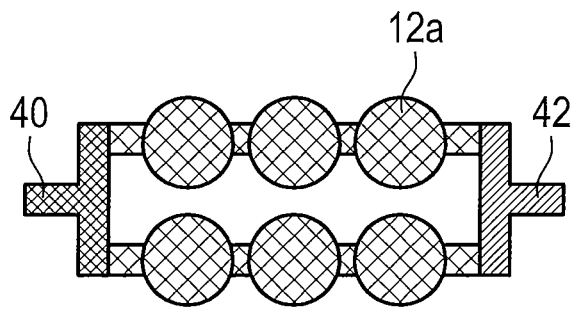
Figure 2D:
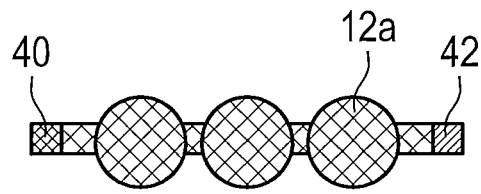

FIGS. 2b to 2d by way of example show three different setup variants in a top view, which are based on the embodiment of the single-use filtration device 10 comprising upright filter capsules 12 as shown in FIG. 2a, whose inflow ports each are arranged at the upper end and whose outflow ports each are arranged at the lower end. In FIGS. 2b-2d (like in FIGS. 3b, 3c, 4a, 4b, 5b, 5c, 6, 7b-7f, 8b-8h and 9a-9c yet to be explained below) the filter capsules 12 are shown only schematically without a housing in order to illustrate the arrangement of the (different) filter capsules 12.

In the variant of FIG. 2b a total of nine filter capsules 12 are inserted, wherein three filter capsules 12 each are arranged one behind the other in a line branch. The three line branches are traversed in parallel and have a common inlet 40 and a common outlet 42. The variant of FIG. 2c has only two parallel line branches, the variant of FIG. 2d only one. In all variants, filter capsules 12 of the same type with the same filters are inserted. The filter capsules of the setups shown in FIGS. 2b to 2d are filter capsules 12 with sterile filters (hereinafter referred to as sterile filter capsules 12a); but there can also be provided filter capsules 12 with prefilters (hereinafter referred to as prefilter capsules 12b).

Figure 3A:
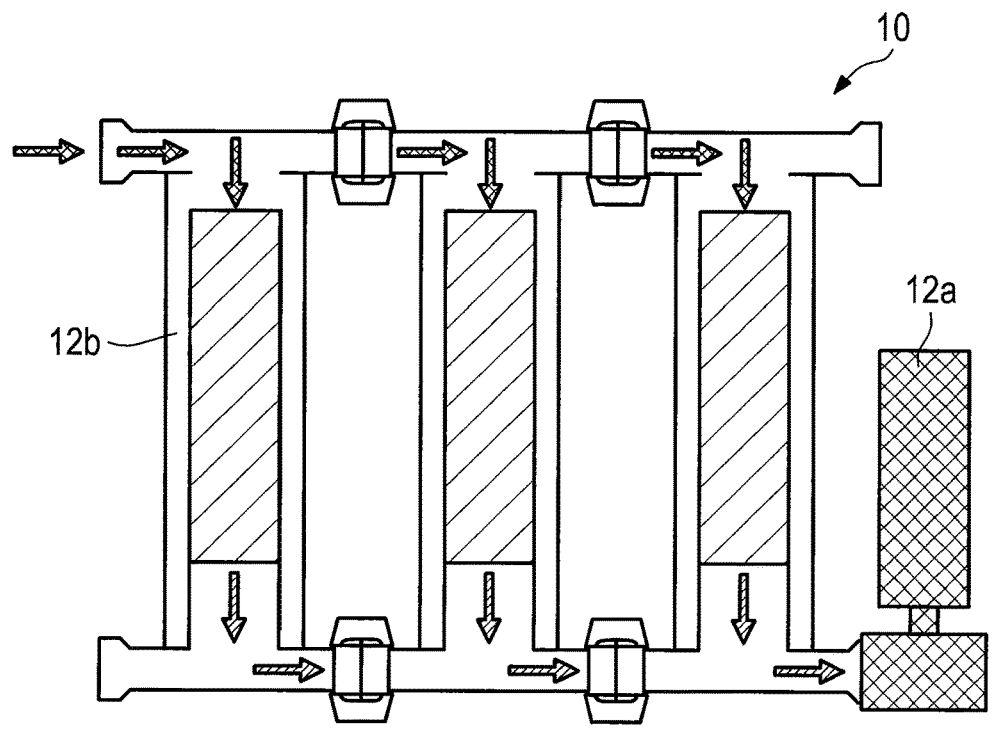
FIGS. 3a to 3c show schematic representations of different variants of a second embodiment of the single-use filtration device according to the invention without a holder in a side view and in a top view, respectively.
Figure 3B:
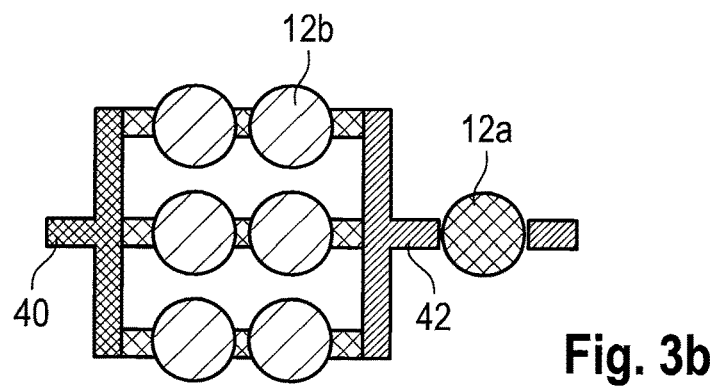
Figure 3C:
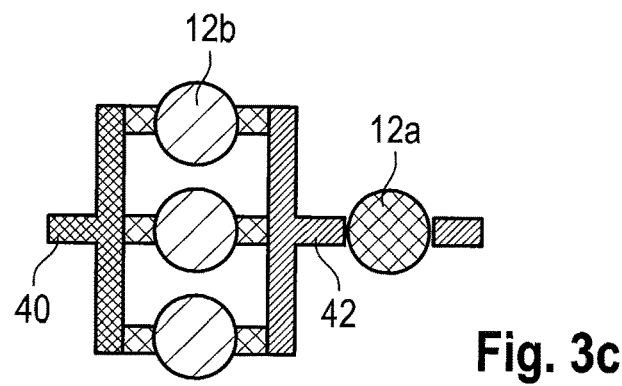

The setups shown in FIGS. 3a to 3c likewise include a plurality of line branches traversed in parallel. However, prefilter capsules 12b are inserted here. Moreover, in the setups of FIGS. 3b and 3c less filter capsules 12 are provided per line branch, namely only two (FIG. 3b) or only one (FIG. 3c). In addition, there is also provided a further filter capsule, here a sterile filter capsule 12a. This sterile filter capsule 12a is arranged behind the joined outlet 42 of the line branches in flow direction, i.e. it is traversed by the filtrate of all line branches.

In the exemplary embodiments of FIGS. 3a to 3c different types of filter capsules 12 are shown. The prefilter capsules 12b have their inflow port and their outflow port at opposite ends of their oblong base body. The type of construction of the sterile filter capsule 12a differs therefrom to the effect that its inflow port and its outflow port are arranged at the same end of the capsule. The base body of the capsule here extends transversely to the—in general mutually opposite—ports. This type of construction is referred to as "T-style".

A filter capsule 12 also can have only one inlet and only one outlet and be integrated into the line preferably horizontally. This type of construction is referred to as "in-line".

In-line and T-style filter capsules have in common that with them a series connection of a plurality of filter capsules can be effected. In the type of construction with series-connected lids a plurality of filter capsules are approached in parallel.

In the setups of FIGS. 3a to 3c the sterile filter capsule 12a each has the function of a control filter, which will be discussed in more detail below.

Figure 4A:
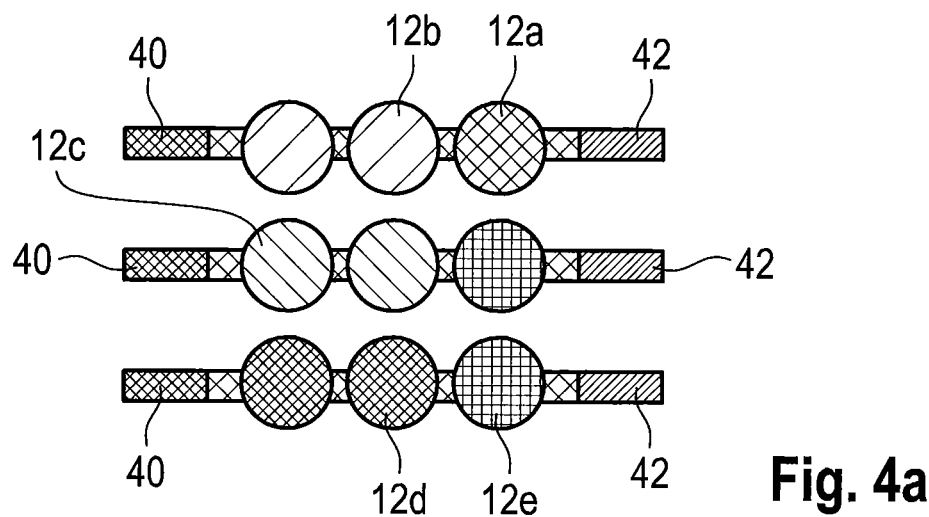
FIGS. 4a and 4b show schematic representations of different variants of a third embodiment of the single-use filtration device according to the invention without a holder in a top view.
Figure 4B:
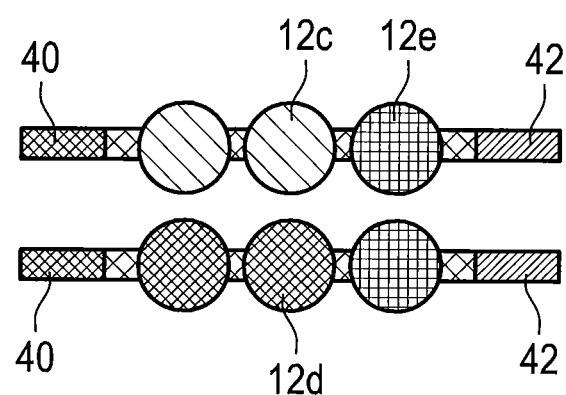

In the setups shown in FIGS. 4a and 4b the single-use filtration device 10 has a plurality of line branches which in so far are independent of each other. The individual line branches hence have separate inlets and separate outlets. Nevertheless, all line branches are integral parts of the preconfigured single-use filtration device 10. The line branches include different types of filter capsules 12a, 12b, 12c, 12d and 12e, wherein the filter capsules can differ in terms of the type of filter (prefilter, sterile filter, etc.), type of construction (series-connected lids, in-line, T-style, etc.) and size.

Due to such a modular construction, a supplier can provide various processes as such or also one, two or more process steps. For carrying out various processes or sub-processes a customer thus can utilize the various setups within a single single-use filtration device 10. The filtration device 10 is particularly space-saving and its installation is particularly time-saving.

Figure 5A:
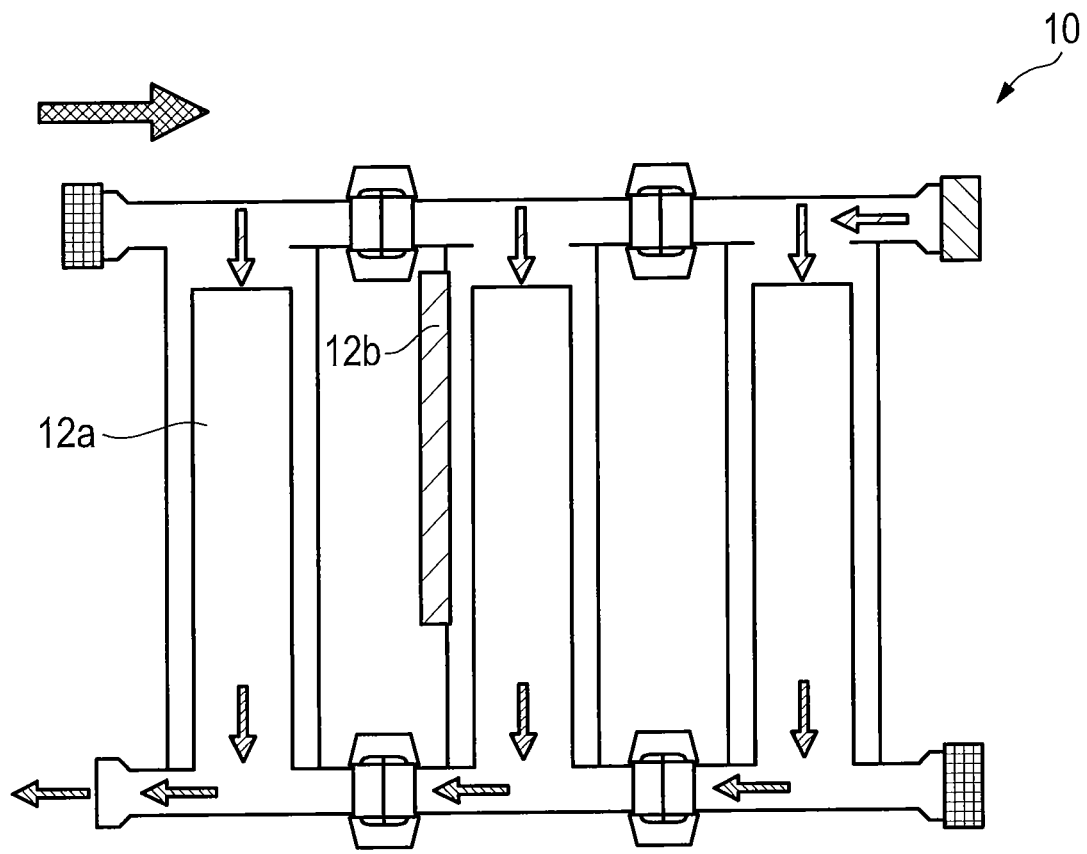
FIGS. 5a to 5c show schematic representations of different variants of a fourth embodiment of the single-use filtration device according to the invention without a holder in a side view and in a top view, respectively.
Figure 5B:
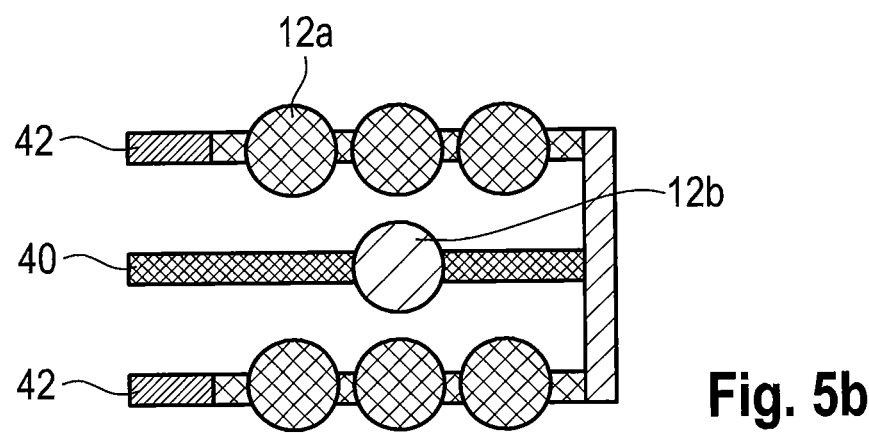
Figure 5C:
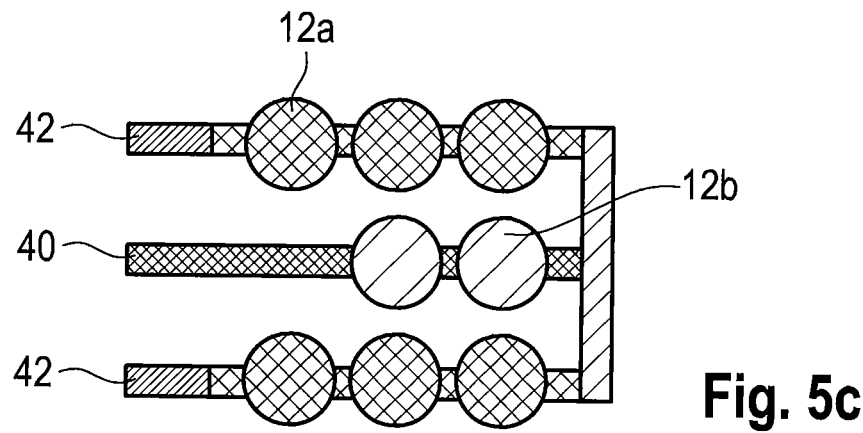
Figure 6:
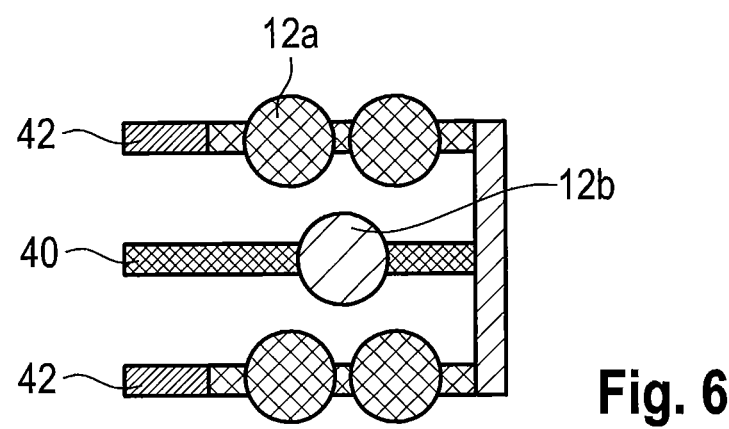
FIG. 6 shows a schematic representation of a fifth embodiment of the single-use filtration device according to the invention without a holder in a top view.

The setups of FIGS. 5a to 5c and of FIG. 6 include a combination of a plurality of sterile filter capsules 12a and one or more upstream prefilter capsules 12b. The prefilter capsules 12b are arranged in an input line branch, from which two line branches with the sterile filters 12a, which are traversed in parallel, branch off. The prefilter capsules 12b here are configured as T-style capsules and with their inflow and outflow ports integrated into the (here upper) input line branch so that the opposite end of the prefilter capsules 12b hangs down. However, a lying arrangement with in-line capsules also is possible.

The setups shown in FIGS. 7a to 7f differ from those of FIGS. 5a to 6b by the arrangement of the inlets 40 and outlets 42 and the number of prefilters 12b and sterile filters 12a. The sterile filter capsules 12a are provided downstream of the prefilter capsules 12b arranged in parallel input line branches. The sterile filter capsules 12a are arranged in a "standing" position, i.e. their inflow and outflow ports are integrated into the lower input line branch so that the opposite end of the sterile filter capsules 12a points upwards. However, a lying arrangement with in-line filter capsules 12 also is possible.

Figure 7A:
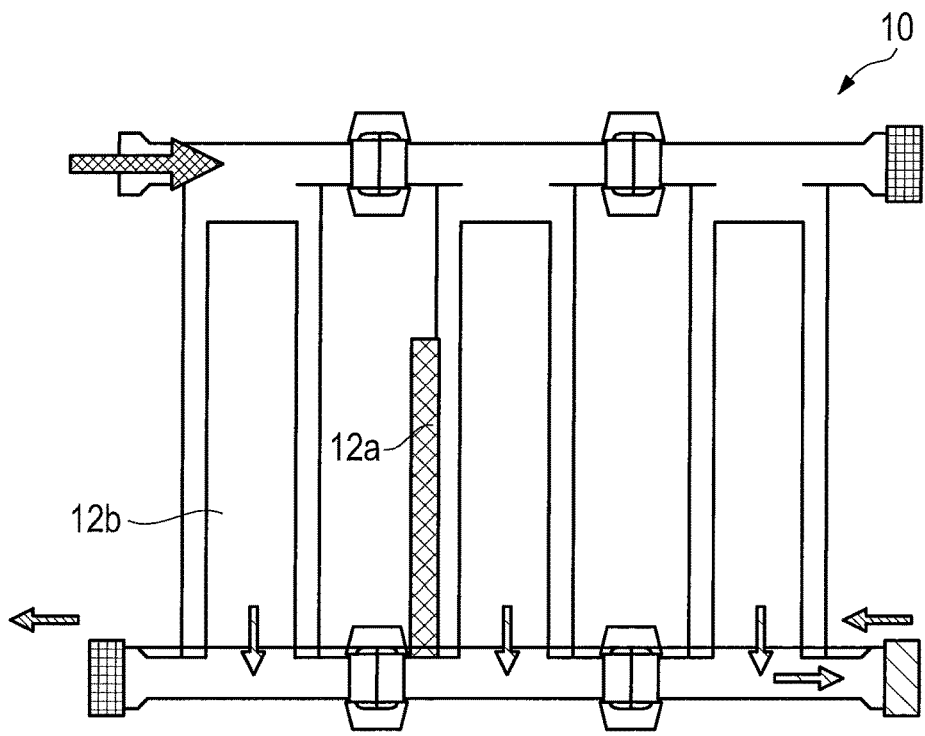
FIGS. 7a to 7f show schematic representations of different variants of a sixth embodiment of the single-use filtration device according to the invention without a holder in a side view and in a top view, respectively.
Figure 7B:
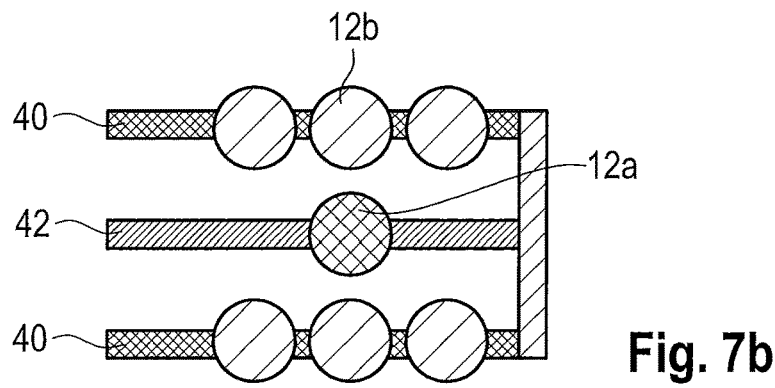
Figure 7C:
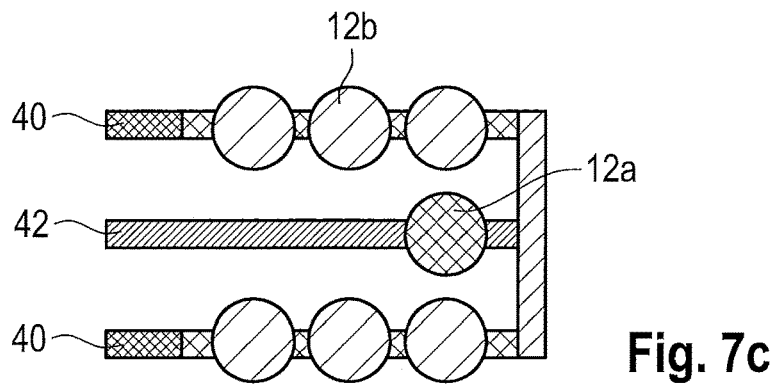
Figure 7D:
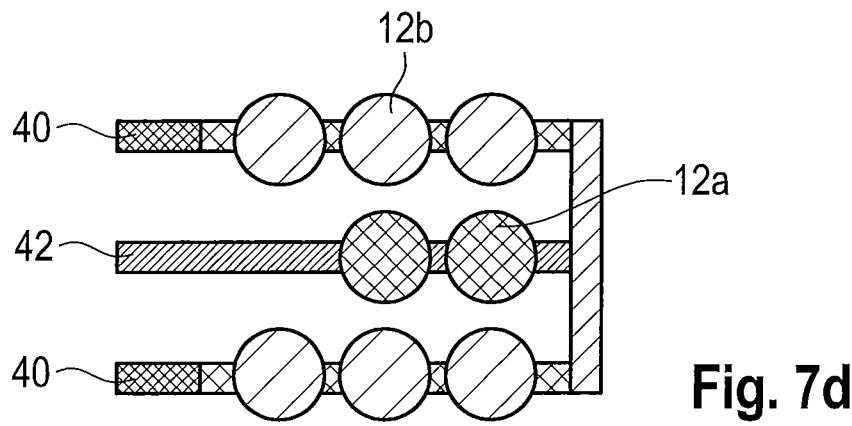
Figure 7E:
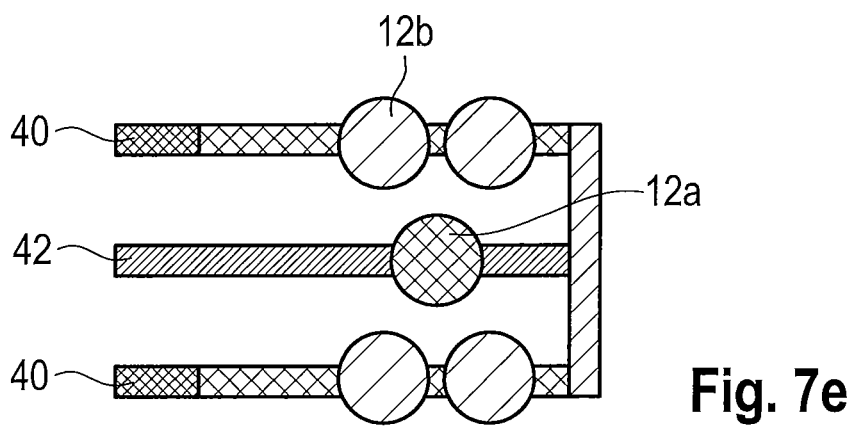
Figure 7F:
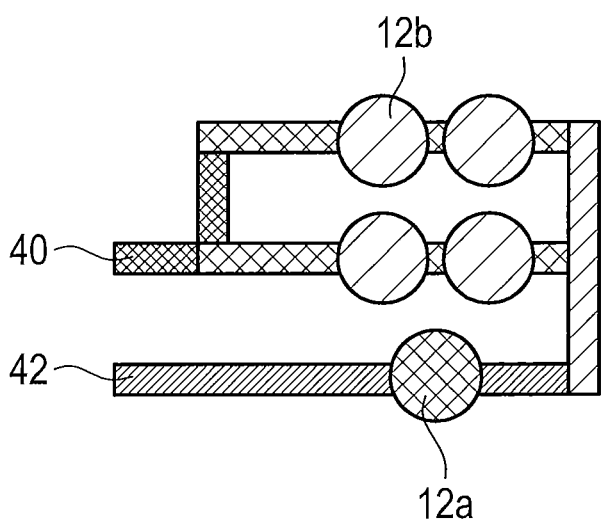

While in the setups of FIGS. 7a to 7e the sterile filter capsules 12a are arranged in a middle line branch, the sterile filter capsule 12a in the setup of FIG. 7f is arranged in an outer, easily accessible line branch.

FIGS. 8a to 8h show various setups in which at least one sterile filter capsule 12a is provided in the form of a T-style or in-line capsule which acts as a control filter means (hereinafter for simplicity referred to as control filter), as will yet be explained below. To the inflow and to the outflow of this control filter an inflow-side first branching member 44 and an outflow-side branching member 46 respectively is connected. To one of the two free ends of the first branching member 44 the outlet of a sterilizable, in particular gamma-sterilizable air filter 50 is connected via an interposed first shut-off valve 48. To one of the two free ends of the second branching member 46 a waste container 54 (waste bag) is connected via an interposed second shut-off valve 52. With the other free end of the first branching member 44 the entire assembly hereinafter referred to as single-use control unit 58, which comprises the control filter, air filter 50, waste container 54, the two branching members 44 and 46 and the first and the second shut-off valve 48, 52, is connected with an outlet port (external port 34) of the remaining single-use filtration device 10 via an interposed third shut-off valve 56. In the final analysis, the other free end of the second branching member 46 represents the filtrate outlet of the single-use filtration device 10. The filtrate outlet can be closed by a fourth shut-off valve 60 which likewise is part of the single-use control unit 58.

Figure 8A:
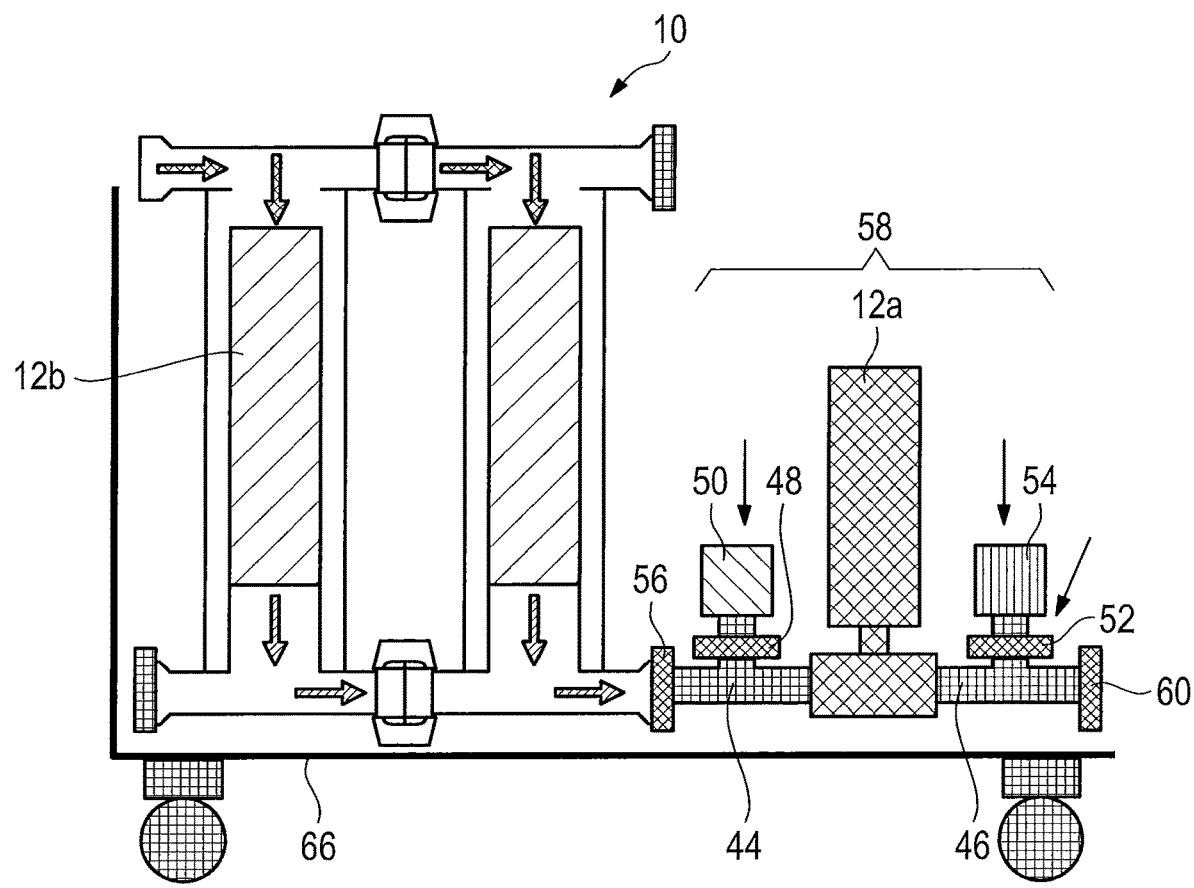
FIGS. 8a to 8h show schematic representations of different variants of a seventh embodiment of the single-use filtration device according to the invention without a holder in a side view and in a top view, respectively.
Figure 8B:
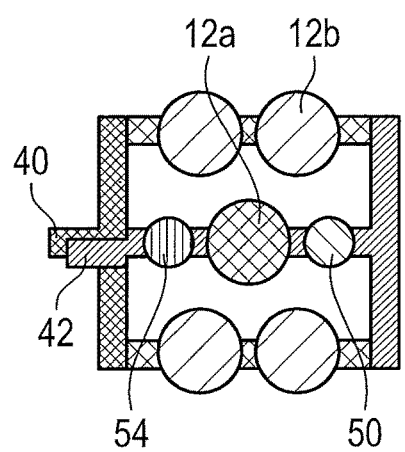
Figure 8C:
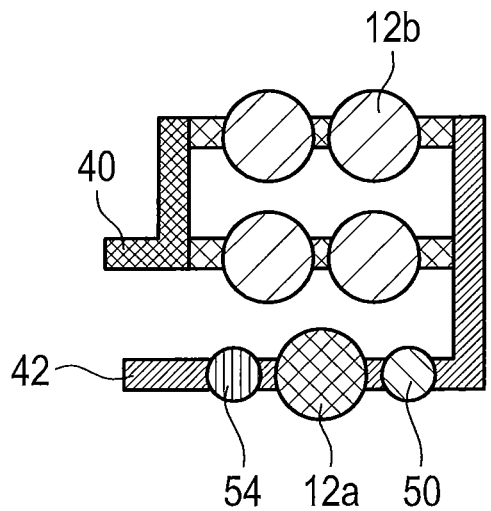
Figure 8D:
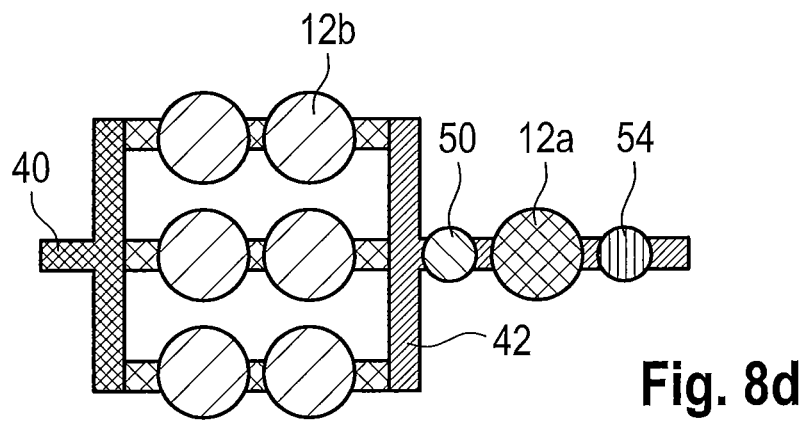
Figure 8E:
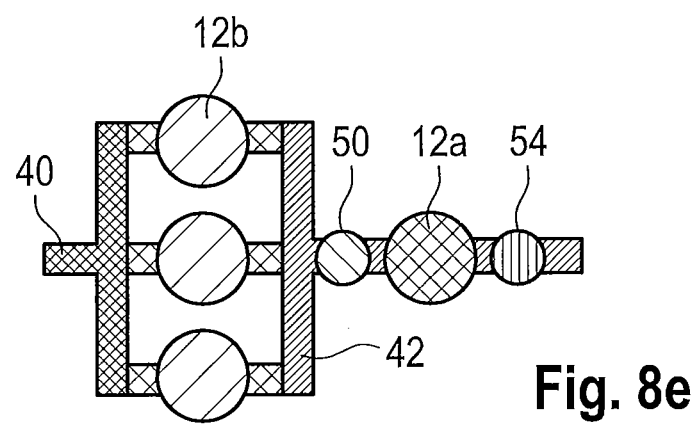
Figure 8F:
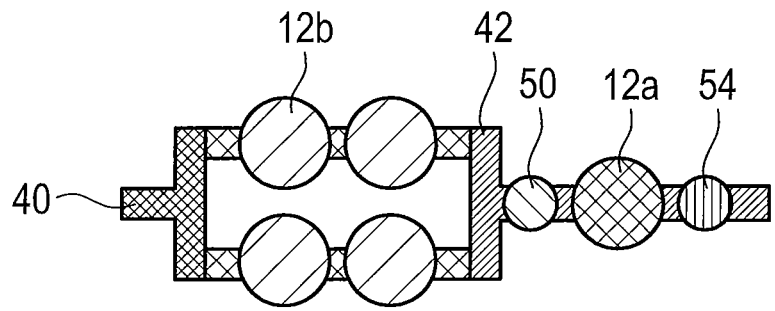

In the setup shown in FIG. 8b the single-use control unit 58 is arranged between two line branches traversed in parallel, which include prefilters 12b. On the other hand, in the setup shown in FIG. 8c the single-use control unit 58 is arranged in an outer, easily accessible line branch of the single-use filtration device 10. Both setups are comparatively space-saving.

FIGS. 8d to 8h show various further setups in which one or more single-use control units 58 arranged in parallel are attached to one or more (common) outlets 42 of the upstream line branches of the single-use filtration device 10. This means that the single-use control units 58 each are arranged outside the raster for the filter capsules 12 specified by the holder 14 of the single-use filtration device 10, wherein the control unit 58 nevertheless is part of the single-use filtration device 10.

Figure 9A:
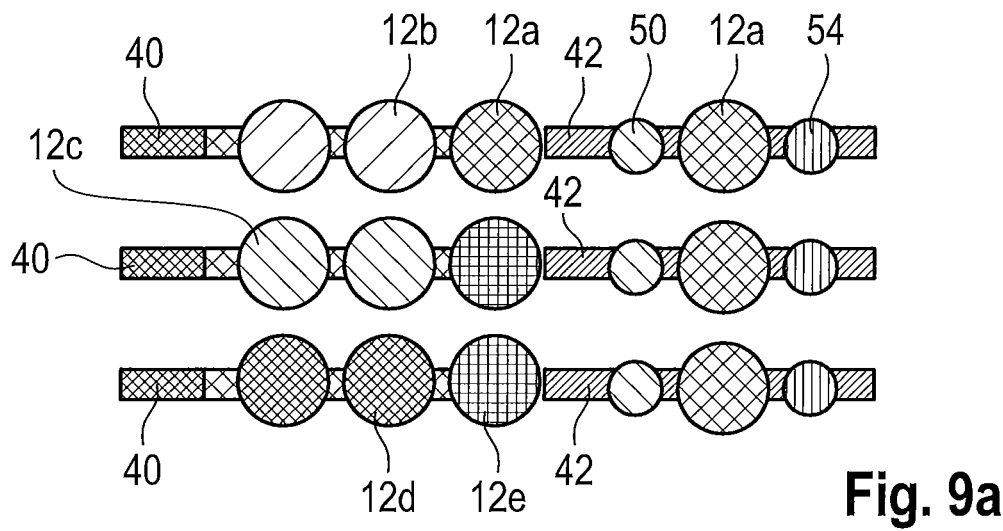
FIGS. 9a and 9c show schematic representations of different variants of an eighth embodiment of the single-use filtration device according to the invention without a holder in a top view.
Figure 9B:
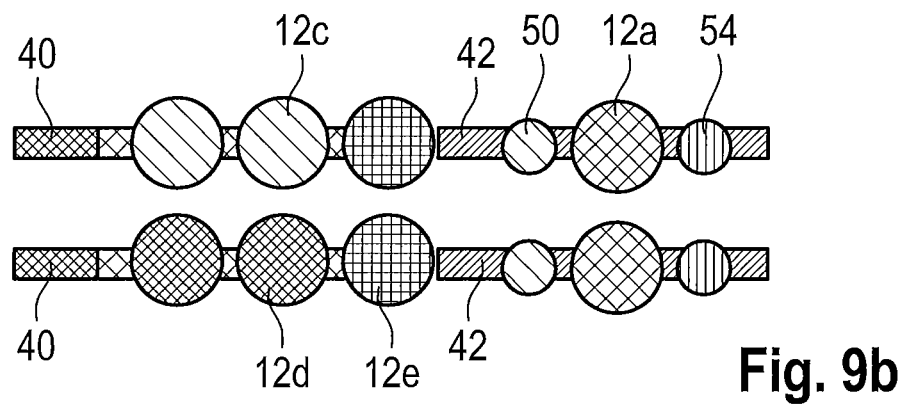
Figure 9C:
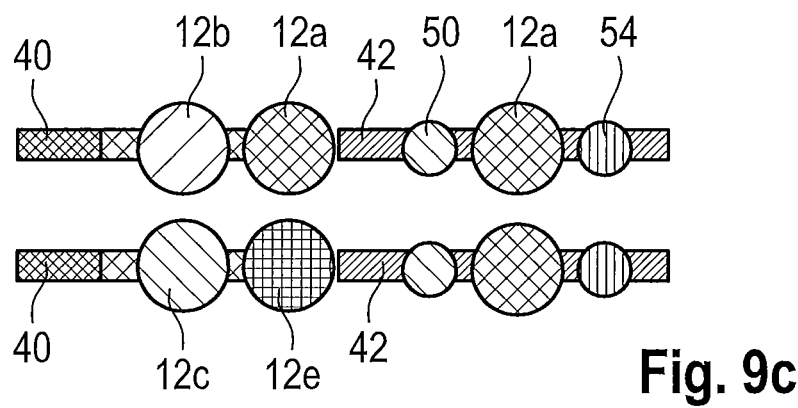

FIGS. 9a to 9c show further setups with a plurality of mutually independent line branches (similar to FIGS. 4a and 4b), which all are integral parts of the preconfigured single-use filtration device 10. The line branches include different types of filter capsules 12a, 12b, 12c, 12d and 12e, wherein the filter capsules can differ in terms of the type of filter (prefilter, sterile filter, etc.), type of construction (in-line, T-style, etc.) and size. To each line branch a separate single-use control unit 58 is attached. This enables a user to correspondingly check the control filter of each separate line.

Figure 10:
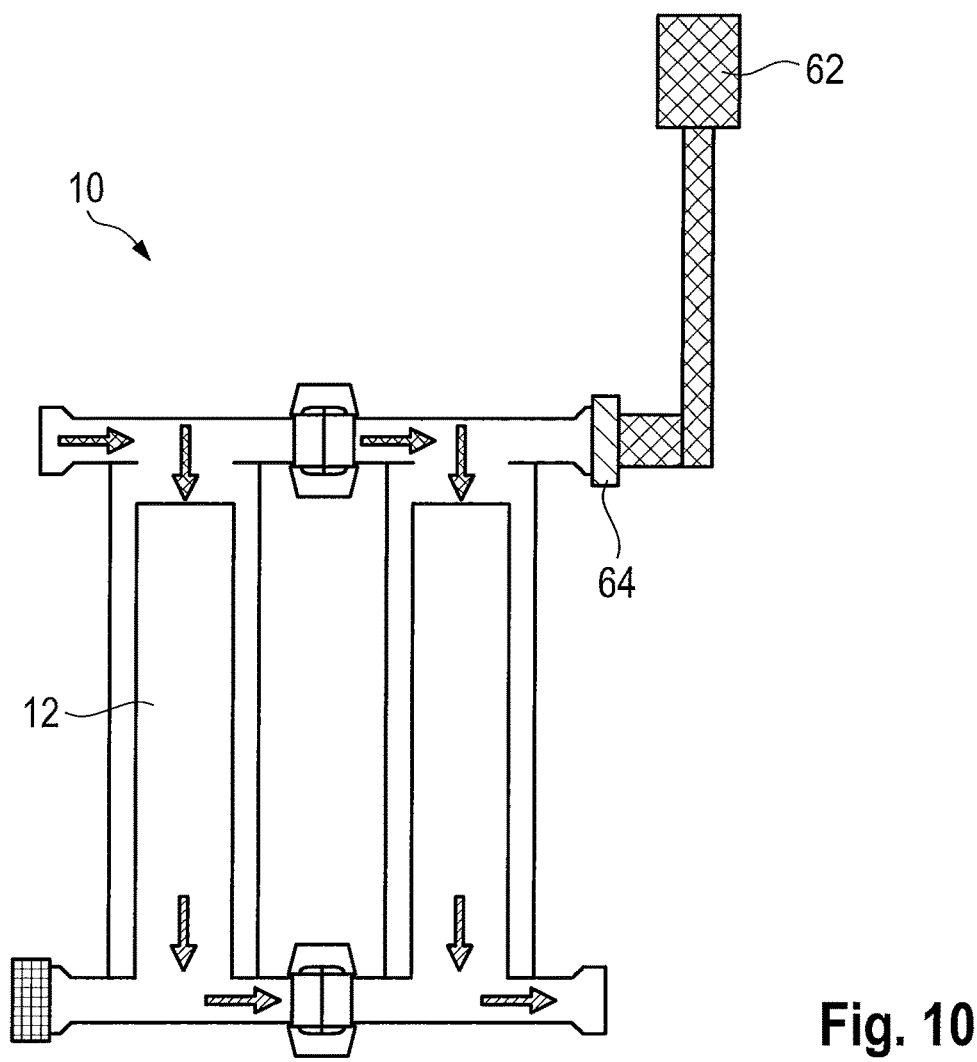
FIG. 10 shows a schematic representation of a ninth embodiment of the single-use filtration device according to the invention without a holder in a side view.

FIG. 10 shows a single-use filtration device 10 without holder 14, in which to an upper external port 34 a sterilizable, in particular gamma-sterilizable air filter 62 is connected. The external port 34 for the air filter 62 need not necessarily be formed by an inflow or outflow device 30, 32. The air filter 62 alone can accomplish the venting of the entire single-use filtration device 10, or a plurality of such air filters 62 are provided at various external ports 34. Between the external port 34 and the inlet of the air filter 62 a separate protective filter 64 is interposed for the protection of the air filter 62.

The above-described setups represent just a selection of a multitude of possible setups. Many more combination possibilities are possible within the single-use filtration device 10.

In the following, special aspects of the invention and particular application possibilities will be explained in detail.

Before the sterilization and the delivery to a customer, the single-use filtration device 10 can be preconfigured as desired. Various types of filter capsules 12 (type of filter, type of construction, size etc.) can be inserted at the points specified by the holder 14. It should be considered that the holder 14 itself can also be configured as desired. For example, it can specify a 3×3 raster just like a 2×3 raster or any other rasters for the filter capsules 12. Many combinations of filter capsules 12 are possible, in particular of prefilter capsules 12b and sterile filter capsules 12a or, such as in a redundant sterile filtration, with a combination of several sterile filter capsules 12a with the same porosity, e.g.

0.2 μm, or a different porosity, e.g. 0.2 μm and 0.1 μm, within the same single-use filtration device 10.

The filter capsules 12 are clamped, welded, screwed, glued or otherwise stably attached to suitable holding means 20.

By means of the conduits 22 and/or the inflow and outflow devices 30, 32 various flow paths with one or more line branches can be defined, which can be traversed one after the other or in parallel. As necessary, line branches connected with each other or separate, mutually independent flow paths (process chains) can be realized by the filter capsules 12 within the single-use filtration device 10.

In this way it is possible in a space-saving way to establish stable, completely presterilizable setups for various processes within the compact single-use filtration device 10.

After a setup agreed upon with the customer has been established in the holder 14, the entire single-use filtration device 10 is packed, sterilized and delivered as a unit ready for operation. The customer can utilize the single-use filtration device 10 immediately after unpacking, as for the desired filtration process no further components must be integrated into the single-use filtration device 10.

As shown in FIG. 8*a* by way of example, the entire single-use filtration device 10 can be arranged on a carriage 66 or on another movable device for an improved local mobility and handling. As mentioned already, the single-use filtration device 10 alternatively or in addition can also include a handle on the holder 14.

The sterile filter capsule 12 used as a control filter in the embodiments of FIGS. 3*a* to 3*c* and 8*a* to 8*h* has the object to ensure as the "last instance" that actually a sterile filtrate has been produced. The sterility of the filtrate is confirmed by passing an integrity test of the control filter.

The control filter is arranged downstream of the filter capsules 12 of the single-use filtration device 10 provided for the actual filtration process for the following reason: When the single-use filtration device 10 is tested for integrity, it cannot necessarily be concluded from an expected total diffusion (ml/min), which results from the setpoint values of all filter capsules 12 or the individual filter candles 28 arranged therein, that all filter capsules 12 or filter candles 28 do not exceed their respective limit value. For example, a (defective) filter candle 28 without integrity can exceed its limit value and one or more other filter candles can fall below their limit value, so that the values balance each other out in so far as in total the expected value for the entire single-use filtration device 10 is not exceeded. Nevertheless, the defective filter candle 28 might let through e.g. bacteria, which would lead to the fact that the filtrate as a whole would not be sterile. Therefore, after the regular filtration a separate control filtration by means of a separate filter capsule 12, in particular a sterile filter capsule 12*a*, is provided, through which the entire filtrate passes in the end. This individual control filter can reliably be tested for integrity as a separate unit without much effort. When the integrity test of the control filter is passed, it can be assumed that the entire filtrate obtained actually is sterile.

Alternatively or in addition to the diffusion measurement the so-called bubble point can also be determined during an integrity test of the control filter. The pores of the filter (in a sterile filtration e.g. 0.2 μm) are filled with a wetting medium, which most easily is accomplished by rinsing the filter capsule 12*a* under pressure. For the test, the filter is slowly pressurized, preferably from the approach flow side. To displace the wetting medium from the pore, a force (pressure difference of the two filter sides) is necessary. This pressure difference is dependent on the pore diameter. The pressure on the filter is increased, and as soon as a continuous exit of air bubbles can be recognized, the pressure is read from the testing device, for example from a manometer. As surface tension, wetting angle and pressure difference are known, the largest pore of the membrane theoretically can be calculated and thus its quality can be determined. Usually, however, the pressure read simply is compared with the limit value indicated by the filter manufacturer.

Depending on the setup, two or more control filters can also be used in parallel.

The control filter is integrated into the single-use filtration device 10, i.e. it is an integral part of the single-use filtration device 10 sterilized already prior to delivery. The control filter hence need not subsequently be connected via tube systems, which would mean an additional expenditure of material and time for establishing a secure and stable connection. An additional holder or the like for fixing the control filter is not needed, as the control filter is delivered as a fixed component.

In the setups shown in FIGS. 8*a* to 9*c* the particular advantage consists in that the control filter (sterile filter capsule 12*a*) integrated into the single-use filtration device 10 can be tested for integrity, without a reconstruction or a disassembly of components of the single-use filtration device 10 being necessary. The integrity test of the control filter can be carried out directly before the intended use of the single-use filtration device 10 (pre-use integrity test) and/or after the use (post-use integrity test).

In the pre-use integrity test, the first shut-off valve 48 to the sterile air filter 50 and the fourth shut-off valve 60 at the filtrate outlet of the single-use control unit 58 are closed. The second shut-off valve 52 to the waste container 54 is opened. After opening the third shut-off valve 56, the filters of the filter capsules 12 including the control filter are wetted with a suitable liquid medium. Excess wetting medium gets into the waste container 54. After wetting the filters, the third shut-off valve 56 is closed again so that the single-use control unit 58 is fluidically separated from the rest of the single-use filtration device 10. The first shut-off valve 48 to the air filter 50 is opened. To the inlet of the air filter 50 a testing device now is connected, by means of which the checks provided for the integrity test, in particular the diffusion measurement and/or the determination of the bubble point of the control filter are carried out. Air sterilized by the sterile air filter 50 is pumped into the single-use control unit 58. The liquid pressed through the control filter during the integrity test gets into the waste container 54 and can be disposed of after the second shut-off valve 52 has been closed. After completion of the pre-use integrity test, the first shut-off valve 48 to the air filter 52 is closed and the third shut-off valve 56 and the fourth shut-off valve 60 are opened. The single-use filtration device 10 including the control filter now is ready for the intended use.

Alternatively or in addition to the pre-use integrity test a post-use integrity test can be carried out in the following way after carrying out the filtration process in order to check whether the control filter is defective. After completion of the filtration process, the third shut-off valve 56 and the fourth shut-off valve 60 at the filtrate outlet are closed. The first shut-off valve 48 to the air filter 50 and the second shut-off valve 52 to the waste container 54 are opened. As described already, the integrity test can now be carried out by means of a testing device connected to the inlet of the air filter 50. Alternatively, the filtrate can be disconnected before the test and a waste container 54 (if required at all) can also be connected to the fourth shut-off valve 60. In this case, the second shut-off valve 52 must be closed and the fourth shut-off valve 60 must be opened for carrying out the post-use integrity test. After completion of the integrity test, all open valves are closed so that no liquid can exit uncontrolled on disposal of the entire single-use filtration device 10.

In a control filter provided downstream of a single-use filtration device according to the prior art via additional tube systems only after the intended use it is not expedient in principle to carry out a pre-use integrity test, as the sterile system would have to be disconnected and the complete single-use filtration device 10 thereby would become non-sterile. A post-use integrity test can be carried out only after the control filter is separated from the tube system provided downstream of the single-use filtration device 10. This involves an additional expenditure of time and work.

Figure 8G:
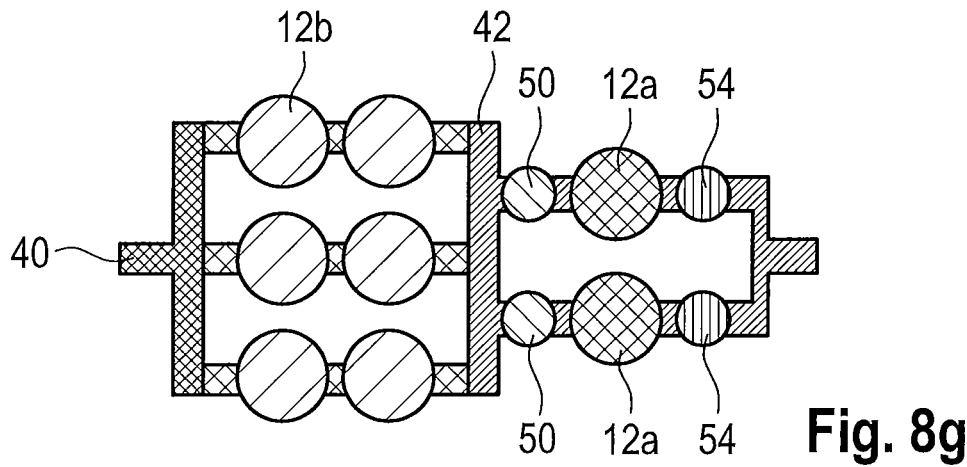
Figure 8H:
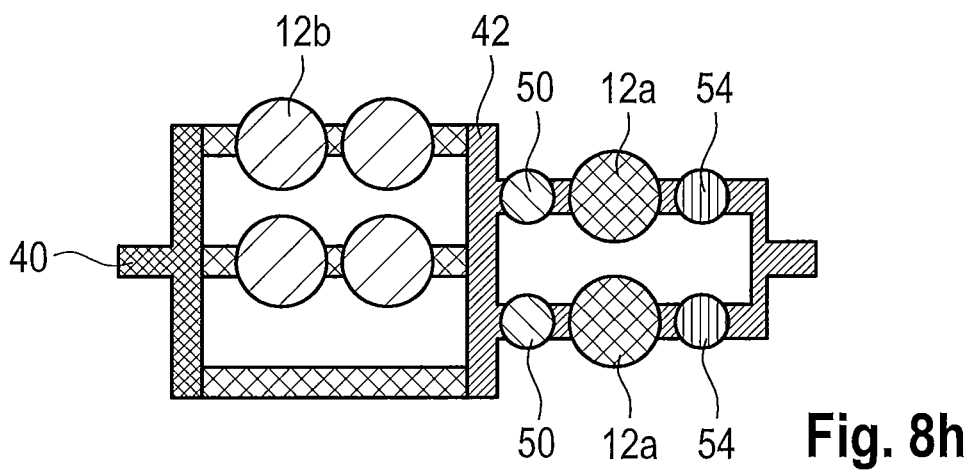

When the filter area of a control filter subsequent to the prefilter capsules 12b and/or sterile filter capsules 12a is not sufficient, it is possible to also provide two or more control filters traversed in parallel downstream of the single-use filtration device 10, as is shown by way of example in FIGS. 8g and 8h. Each of the control filters connected in parallel can individually be subjected to a pre-use integrity test and/or a post-use integrity test. The same applies for the comparable setups shown in FIGS. 9a to 9c, in which a plurality of control filters are provided which each are attached to an individual process chain of the single-use filtration device 10.

In the single-use filtration device 10, independent of its concrete setup, a sterilizable, in particular gamma-sterilizable air filter 62, usually is provided at one of the upper external ports 34 for venting purposes, as is schematically shown in FIG. 10. Although a plurality of such air filters 62 can be provided in principle, only one central air filter 62 for all filter capsules 12 is assumed in the following for reasons of simplicity, which filter capsules are involved in the intended filtration process (hence excluding a possible control filter which is arranged in a single-use control unit 58 together with a separate air filter 50). The air filter 62 typically is configured as a filter candle with a pleated air filter membrane arranged between two supporting fleece layers.

When filling the single-use filtration device 10 with water or another liquid, care must be taken in principle that liquid can get to the air filter 62. This liquid can form a kind of film on the supporting fleece and thereby block the air filter 62. Due to blocking of the air filter 62, no or only little throughput of air is possible, which limits the basic function of the air filter 62. It should also be taken into account that the air filter 62 also is provided to test the involved filter capsules 12 or the entire single-use filtration device 10 for integrity before commencement or after completion of the filtration process. Due to blocking of the air filter, problems can occur in such a test.

Known filtration devices are complicated by the fact that the air filter typically is connected to the single-use filtration device 10 by a fabric-reinforced hose. The use of a fabric-reinforced hose is necessary due to the partly very high test pressures of the liquid filters or the very high process pressures. Because of the fabric-reinforced hose, however, the operator cannot visually identify whether water or other filtration solutions move towards the air filter. Timely shutting off the filtration process or sealing off the air filter by means of a valve or the like thus is not easily possible.

In the following, several possibilities to avoid the problems of an air filter 62 blocked by water or filter medium are presented. The individual solution aspects can also be combined with each other as desired.

According to a first solution aspect a protective filter 64 is interposed between the external port 34 and the inlet of the air filter 62, as shown in FIG. 10. The protective filter 64 is configured as a flat filter without supporting fleeces or the like, wherein the air filter membrane can be formed of polyvinylidene fluoride (PVDF), polyethylene (PE), hydrophobic polyethersulfone (PESU) or polytetrafluoroethylene (PTFE). As the protective filter 64 has no supporting fleeces, the risk of blocking is minimized. The operator hence need not take care of a possible blocking.

According to a second solution aspect, part of the flow path between the external port 34 and the air filter 62 is configured as a stable sight glass. As already mentioned above, sight glass is understood to be a transparent tubular portion which in particular can be formed of glass or a transparent plastic material. The sight glass provides for a visual inspection by the operator, who can take measures as soon as he recognizes that water or another medium rises to the air filter 62. The adjusted volume flow, the length of the line to the air filter 62 and the position of the sight glass in this line determine the period of time left for the operator to take measures before the water or medium reaches the air filter 62.

According to a third solution aspect, at least one indicator which reacts to water is arranged in the flow path between the external port 34 and the air filter 62. Such water-contact indicators are available as adhesive tapes which turn red on contact with water or are based on blue gel (silica gel) which turns pale pink. Such an indicator provides for a visual inspection by the operator, who possibly can take suitable measures.

According to a fourth solution aspect an at least partly transparent standard silicone tube is provided, which is surrounded by a likewise transparent supporting envelope. As an envelope e.g. tear-resistant films, a stable sheath or a tightly fitting tube can be considered. The envelope prevents that the standard silicon tube, which actually is permitted only for low pressures, bursts at high pressures. Due to the transparent materials of tube and envelope a visual inspection by the operator nevertheless is possible.

Figure 11:
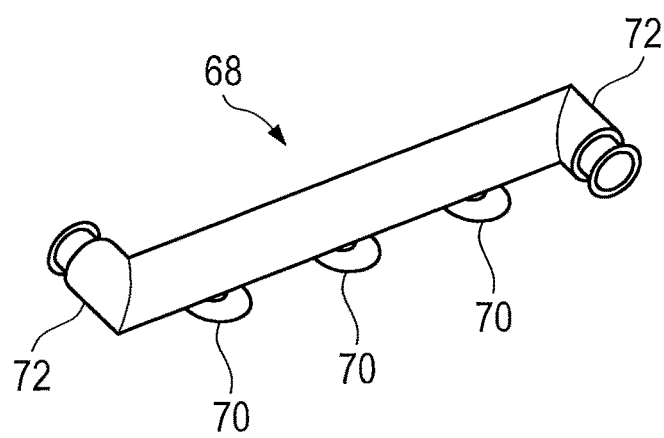
FIG. 11 shows a perspective representation of a first embodiment of the pipe manifold piece according to the invention.

FIG. 11 by way of example shows a rigid plastic pipe manifold piece 68 which can be employed in the single-use filtration device 10, but also in other single-use devices, in particular in the biopharmaceutical field.

It is the main purpose of the pipe manifold piece 68 to produce a flow connection between two single-use components or a flow distribution over several single-use components. The basically tubular pipe manifold piece 68 in particular replaces conventional tube connections and is made of a sterilizable, in particular gamma-sterilizable plastic material and is autoclavable. The plastic material can be either opaque or transparent. The pipe manifold piece 68 is designed such that it safely withstands the required test pressures (e.g. in the order of 10 bar).

As compared to conventional tube connections and also known simple connecting pieces, the pipe manifold piece 68 which according to the exemplary embodiment shown in FIG. 11 has three branchings 70 is configured with a strongly bent flow path. More exactly, the pipe manifold piece 68 here each has a bend 72 in the form of a 90° kink at its two longitudinal ends. The bends 72 hence are not obtained by assembling individual parts, but are already part of the pipe manifold piece 68.

Figure 12A:
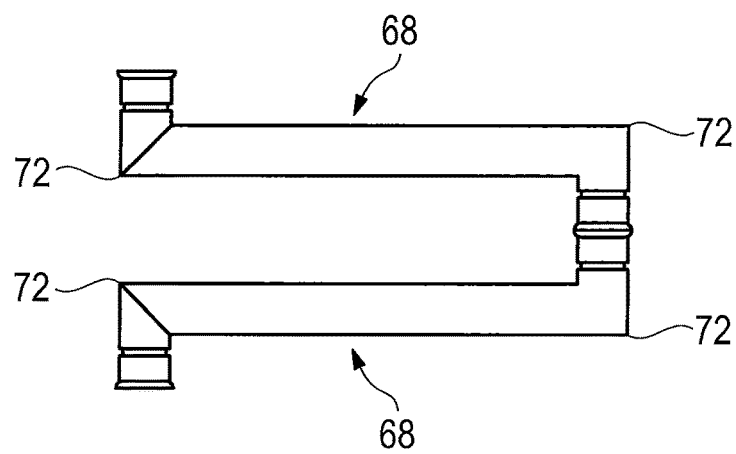
FIGS. 12a and 12b show a comparison between a combination of pipe manifold pieces according to the invention and a combination of conventional pipe manifold pieces in a top view.
Figure 12B:
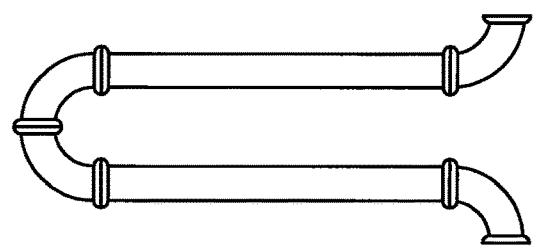

FIGS. 12a and 12b show a comparison between a combination of two pipe manifold pieces 68 (FIG. 12a) and a combination of conventional pipe manifold pieces (FIG. 12b), as they are each needed for the connection of six filter capsules 12 to the branchings 70. The comparison shows that in contrast to the combination of conventional pipe manifold pieces, only two pipe manifold pieces 68 must be connected with each other and a significant saving of installation space is achieved.

The connection of two pipe manifold pieces 68 for example can be effected by means of TRI-clamp connections. At the ends of the pipe manifold piece 68 or its branchings 70 sterile connectors can also be mounted directly. Furthermore, other types of connection are also possible, such as e.g. screwing or welding. The connections in all cases are so pressure-resistant that they withstand the required test pressures. As less connecting points are present than in combinations according to the prior art, there is no risk that the pipe manifold pieces 68 twist against each other. Thus, the mechanical load of the filter capsules 12 is minimized.

Of course, other embodiments of the pipe manifold piece 68 with only one or several, possibly also differently extending integrated bends 72 and/or branchings 70 are possible, which have the same and possibly even further advantages in the overall context.

In principle, valves or other components can be connected directly to the open ends or the branchings 70 of the pipe manifold pieces 68 so that the core of a single-use filtration device 10 can be constructed without tubes and thus is distinctly more pressure-resistant.

Figure 13:
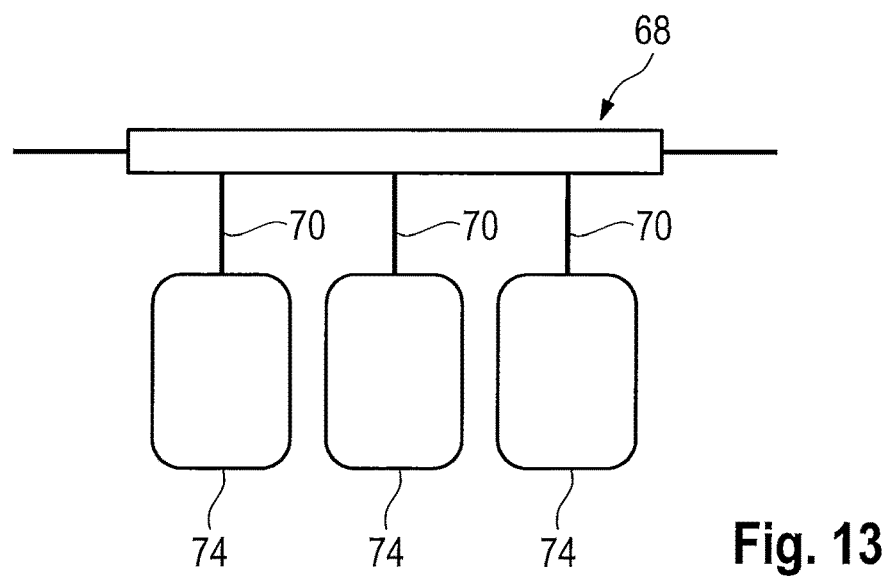
FIG. 13 schematically shows an arrangement of the pipe manifold piece according to the invention with single-use containers.

FIG. 13 by way of example shows another possible application of the pipe manifold piece 68 in conjunction with single-use containers 74, e.g. in the form of bags.

As mentioned already, the different aspects of the invention can be combined with each other in any way, as far as expedient.

The use of the different embodiments of the single-use filtration device 10 and its components, in particular of the pipe manifold piece 68 according to the invention, is not limited to the (bio)pharmaceutical field.

LIST OF REFERENCE NUMERALS 10 single-use filtration device
12 filter capsule
12a sterile filter capsule
12b prefilter capsule
12c-12e other filter capsules
14 holder
16 side wall
18 transverse strut
20 holding means
22 conduit
24 branching
26 standing foot
28 filter candle
30 inflow device
32 outflow device
34 external port
36 connection component
38 closure
40 inlet
42 outlet
44 first branching member
46 second branching member
48 first shut-off valve
50 air filter for integrity test
52 second shut-off valve
54 waste container
56 third shut-off valve
58 single-use control unit
60 fourth shut-off valve
62 air filter for venting
64 protective filter
66 carriage
68 pipe manifold piece
70 branching
72 bend
74 single-use container

The invention claimed is:

1. A single-use filtration device, comprising:
a plurality of single-use filter capsules connected with each other by rigid lines, at least part of which are mounted in a raster specified by a universal holder, wherein the filter capsules selected with regards to type of filter, type of construction and/or size, and/or connections of the filter capsules, are preconfigured for a filtration process;
a sterilizable air filter arranged at an upper external port of the single-use filtration device for venting the single-use filtration device; and
at least one indicator, which reacts to water, arranged in a flow path between the external port and the air filter, wherein part of the flow path between the external port and the air filter is formed by an at least partly transparent silicone tube which is surrounded by a transparent supporting envelope.

2. The single-use filtration device according to claim 1, characterized in that at least some of the filter capsules differ in terms of the type of the filter, the type of the construction and/or the size.

3. The single-use filtration device according to claim 1, characterized in that the lines form a plurality of line branches with associated filter capsules, which are traversed one after the other or in parallel.

4. The single-use filtration device according to claim 1, characterized in that the lines form at least two separate, mutually independent line branches with associated filter capsules.

5. The single-use filtration device according to claim 3, characterized in that the raster is a 3×3 raster for a maximum of nine filter capsules, and the lines are preconfigured such that three or less filter capsules arranged in a row of the raster belong to a line branch.

6. The single-use filtration device according to claim 3, characterized in that at least two parallel line branches have a common inlet and/or a common outlet.

7. The single-use filtration device according to claim 1, characterized in that all filter capsules are sterile filter capsules.

8. The single-use filtration device according to claim 1, characterized in that all filter capsules are prefilter capsules.

9. The single-use filtration device according to claim 1, characterized in that a combination of at least one sterile filter capsule and at least one prefilter capsule is provided.

10. The single-use filtration device according to claim 1, characterized in that in a subsequent line branch a control filter means in a form of a sterile filter capsule is arranged.

11. The single-use filtration device according to claim 1, characterized in that, in a plurality of subsequent parallel line branches, a control filter means, in a form of a sterile filter capsule each, is arranged.

12. The single-use filtration device according to claim 10, characterized in that the control filter means is part of an assembly which is provided for a separate integrity test of the control filter means and comprises the sterilizable air filter.

13. The single-use filtration device according to claim 12, characterized in that, to an inflow and to an outflow of the control filter means, an inflow-side first branching member and an outflow-side second branching member is connected, respectively, wherein the first branching member has two free ends and, to one of the two free ends of the first branching member, an outlet of the sterilizable air filter is connected via an interposed first shut-off valve, wherein to one of the two free ends of the second branching member a waste container optionally is connected via an interposed second shut-off valve, wherein with the other of the two free ends of the first branching member the assembly comprising the control filter means, the air filter, the optional waste container, the first and the second shut-off valve and the two branching members is connected with an external port of the single-use filtration device via an interposed third shut-off valve.

14. The single-use filtration device according to claim 13, characterized in that the other free end of the second branching member forms a filtrate outlet of the single-use filtration device, which can be closed by a fourth shut-off valve.

15. The single-use filtration device according to claim 10, characterized in that the control filter means is arranged in an outer line branch.

16. The single-use filtration device according to claim 10, characterized in that the control filter means is arranged outside the specified raster for the filter capsules.

17. The single-use filtration device according to claim 1, characterized in that between the external port and an inlet of the air filter a hydrophobic protective filter is interposed for the protection of the air filter.

18. The single-use filtration device according to claim 17, characterized in that the protective filter is configured as a flat filter having a protective filter membrane without supporting fleeces, wherein the protective filter membrane is formed of polyvinylidene fluoride (PVDF), polyethylene (PE), hydrophobic polyethersulfone (PESU) or polytetrafluoroethylene (PTFE).

19. A single-use filtration device, comprising:
a plurality of single-use filter capsules connected with each other by rigid lines, at least part of which are mounted in a raster specified by a universal holder, wherein the filter capsules selected with regards to type of filter, type of construction and/or size, and/or connections of the filter capsules, are preconfigured for a filtration process of a liquid medium; and
a sterilizable air filter arranged at an upper external port of the single-use filtration device for venting the single-use filtration device;
wherein the air filter comprises an air filter membrane and a fleece supporting the air filter membrane;
wherein the air filter is sterilizable by means of gamma radiation; and
wherein part of a flow path between the external port and the air filter is configured as a sight glass.

20. A single-use filtration device, comprising:
a plurality of single-use filter capsules connected with each other by rigid lines, at least part of which are mounted in a raster specified by a universal holder, wherein the filter capsules selected with regards to type of filter, type of construction and/or size, and/or connections of the filter capsules, are preconfigured for a filtration process of a liquid medium; and
a sterilizable air filter arranged at an upper external port of the single-use filtration device for venting the single-use filtration device;
wherein the air filter comprises an air filter membrane and a fleece supporting the air filter membrane;
wherein the air filter is sterilizable by means of gamma radiation; and
wherein, in a flow path between the external port and the air filter at least one indicator is arranged, which reacts to water.

21. The single-use filtration device according to claim 1, characterized by at least one single-use pipe manifold piece made of sterilizable plastic material characterized in that it is formed integrally as one piece and includes at least one branching and/or at least one bend.

22. The single-use filtration device of claim 19, wherein the sight glass allows visual inspection by an operator for recognizing that water or another medium rises to the air filter.

23. The single-use filtration device of claim 22, wherein a position of the sight glass determines a period of time left for the operator to take measures before the water or medium reaches the air filter.

24. The single-use filtration device of claim 20, wherein the at least one indicator allows visual inspection by an operator for recognizing that water or another medium rises to the air filter.

* * * * *